(12) United States Patent
Williams

(10) Patent No.: US 10,828,026 B2
(45) Date of Patent: Nov. 10, 2020

(54) TILTABLE ANVIL ASSEMBLY

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 170 days.

(21) Appl. No.: 16/038,318

(22) Filed: Jul. 18, 2018

(65) Prior Publication Data

US 2019/0046180 A1    Feb. 14, 2019

Related U.S. Application Data

(60) Provisional application No. 62/542,338, filed on Aug. 8, 217.

(51) Int. Cl.
| | |
|---|---|
| *A61B 17/068* | (2006.01) |
| *A61B 17/115* | (2006.01) |
| *A61B 17/00* | (2006.01) |
| *A61B 90/00* | (2016.01) |
| *A61B 17/3205* | (2006.01) |
| *A61B 17/072* | (2006.01) |

(52) U.S. Cl.
CPC ........ *A61B 17/068* (2013.01); *A61B 17/1152* (2013.01); *A61B 17/1155* (2013.01); *A61B 17/32053* (2013.01); *A61B 2017/00292* (2013.01); *A61B 2017/07257* (2013.01); *A61B 2090/035* (2016.02)

(58) Field of Classification Search
CPC .............. A61B 17/068; A61B 17/1152; A61B 17/1155
USPC ........................................... 227/175.1–180.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Dec. 10, 2018 issued in EP Appln. No. 18187793.

(Continued)

*Primary Examiner* — Nathaniel C Chukwurah
(74) *Attorney, Agent, or Firm* — Carter, DeLuca & Farrell LLP

(57) ABSTRACT

A tiltable anvil assembly is provided that includes an anvil head assembly that is tiltable from an operative position to a post-fired tilted position after firing of a circular stapler to minimize the profile of the anvil head assembly during removal of the anvil head assembly from a body lumen of a patient. In order to simplify removal of a tissue doughnut from the anvil head assembly after firing, the anvil assembly includes locking structure to retain the anvil head assembly in a post-fired doughnut removal position.

19 Claims, 9 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 * | 10/2005 | Aranyi ............. A61B 17/072 227/176.1 |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |

(56) References Cited

U.S. PATENT DOCUMENTS

| | | |
|---|---|---|
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,016,547 B2 * | 4/2015 | Mozdzierz ......... A61B 17/1155 227/179.1 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2005/0205639 A1 * | 9/2005 | Milliman ............. A61B 17/115 227/175.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0230581 A1 * | 9/2008 | Marczyk ............. A61B 17/115 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0038401 A1 * | 2/2010 | Milliman ............. A61B 17/1114 227/175.1 |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 * | 12/2012 | Qiao .................... A61B 17/115 227/175.1 |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0092720 A1 * | 4/2013 | Williams ......... A61B 17/07207 227/181.1 |
| 2013/0105544 A1 | 5/2013 | Mozdzierz et al. |
| 2013/0105546 A1 | 5/2013 | Milliman et al. |

(56) References Cited

U.S. PATENT DOCUMENTS

| | | |
|---|---|---|
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1* | 7/2013 | Olson .................. A61B 17/068 227/180.1 |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367444 A1* | 12/2014 | Williams ............ A61B 17/1155 227/175.1 |
| 2015/0069108 A1* | 3/2015 | Williams ............ A61B 17/1114 227/175.1 |
| 2015/0129635 A1* | 5/2015 | Williams ........... A61B 17/1155 227/177.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3031408 A1 | 6/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2017096502 A1 | 6/2017 |

OTHER PUBLICATIONS

European Office Action dated Dec. 3, 2019, issued in EP Appln. No. 18187793, 4 pages.

* cited by examiner

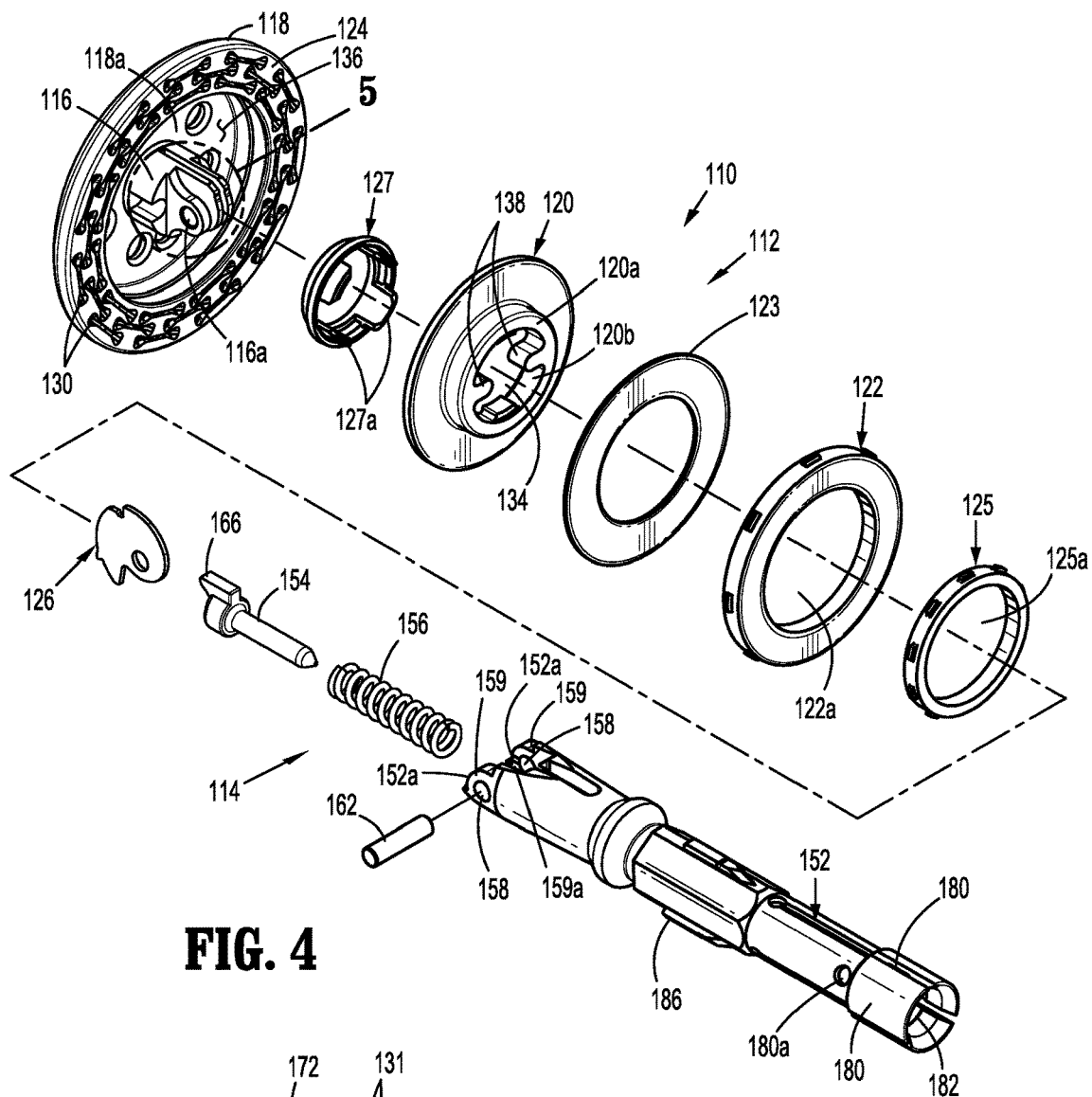
FIG. 4
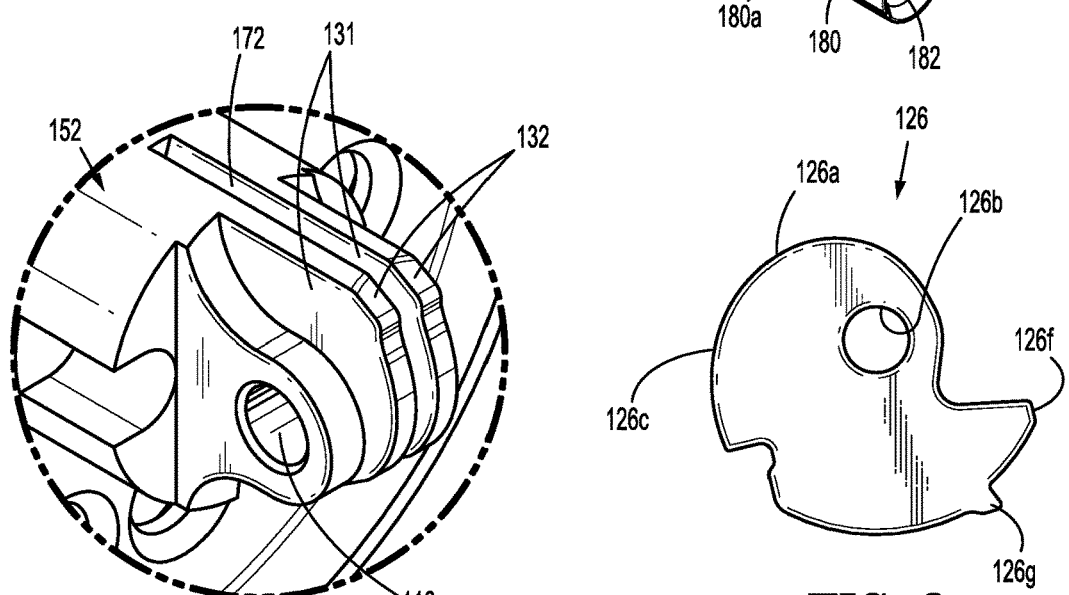
FIG. 5
FIG. 6

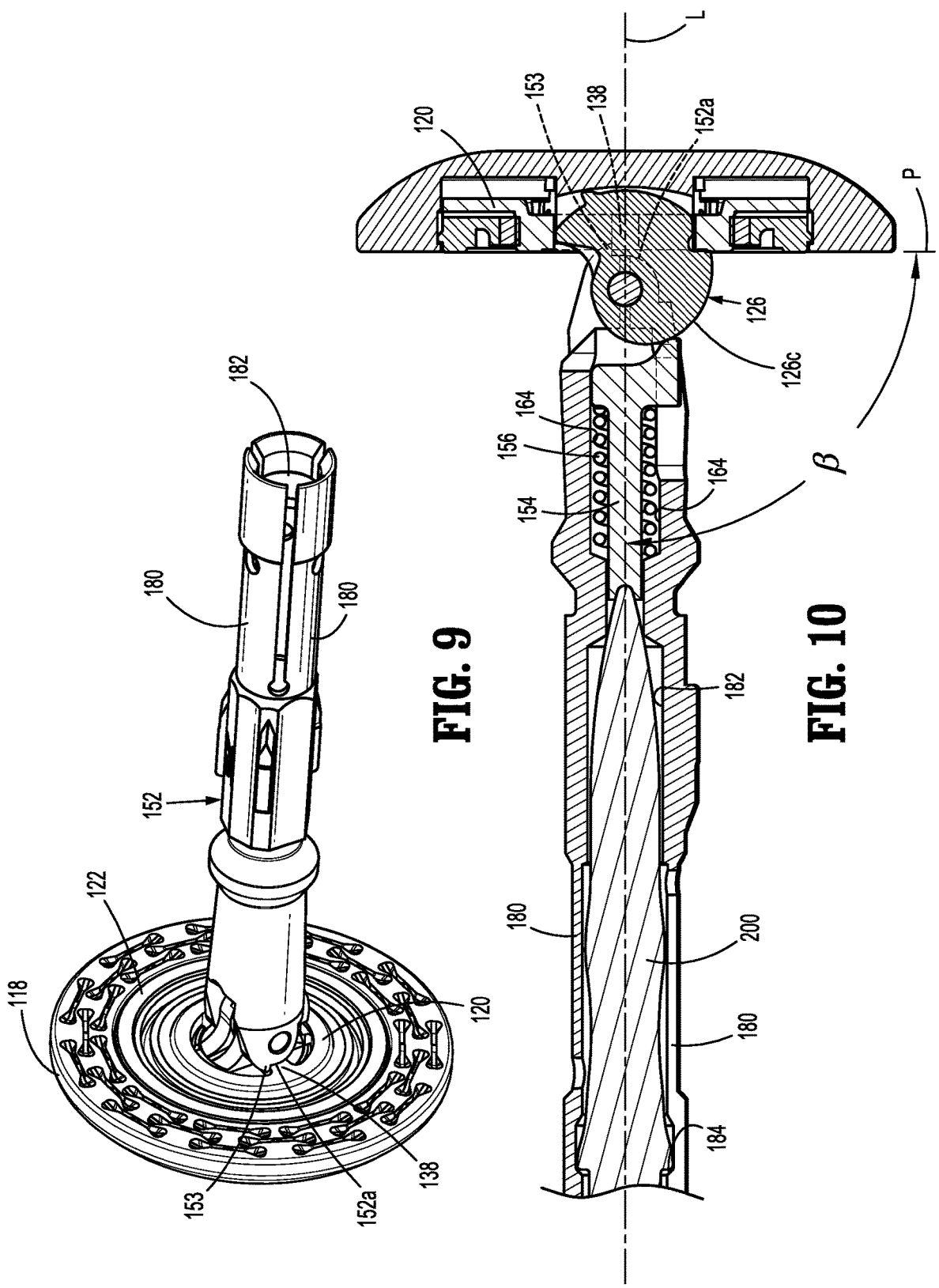

TILTABLE ANVIL ASSEMBLY

CROSS-REFERENCE TO RELATED APPLICATIONS

This application claims the benefit of and priority to U.S. Provisional Patent Application Ser. No. 62/542,338 filed Aug. 8, 2017, the entire disclosure of which is incorporated by reference herein.

BACKGROUND

1. Technical Description

The present disclosure is directed to an anvil assembly that includes a tiltable anvil head and, more particularly, to an anvil assembly including a tiltable anvil head that is movable from a post-fired tilted position to a doughnut removal position and includes structure to retain the anvil head assembly in the doughnut removal position.

2. Background of Related Art

Circular staplers that have anvil assemblies that include an anvil head that can tilt from a tilted position to an operative position during insertion of the anvil assembly into a patient and/or from an operative position to a tilted position during removal of the anvil assembly from the patient are well known. By tilting the anvil head of the anvil assembly during insertion and/or removal of the anvil head from a lumen of the patient, a profile of the anvil head can be reduced to minimize trauma to the patient.

In circular staplers that have an anvil assembly with an anvil head that is tilted after firing of the circular stapler to a post-fired tilted position, the anvil head is typically biased towards the post-fired tilted position by a biasing member. In the post-fired tilted position, it is difficult to remove a tissue doughnut from the anvil head. Thus, the anvil head must be manually pivoted back towards the operative position and retained in this position during removal of the tissue doughnut from the anvil head.

A continuing need exists in the stapler arts for a circular stapler that includes an anvil assembly with an anvil head that can be retained in a position to facilitate easy removal of a tissue doughnut from the anvil head after a circular stapler is fired.

SUMMARY

One aspect of the disclosure is directed to a method of treating tissue including inserting an anvil assembly having an anvil center rod assembly and an anvil head assembly into a vessel lumen in a pre-fired tilted position in which a plane defined by an anvil surface of the anvil head assembly and a longitudinal axis of the anvil center rod assembly define an angle β of less than thirty degrees (30°); moving the anvil head assembly from the pre-fired tilted position to an operative position in which the angle β is ninety degrees (90°); clamping tissue between the anvil surface of the anvil head assembly and a staple cartridge of a circular stapler; firing the circular stapler to advance staples through the tissue and into the anvil head assembly and cutting the tissue with an annular knife; moving the anvil head assembly from the operative position to a post-fired tilted position in which the angle β is less than thirty degrees (30°); moving the anvil head assembly from the post-fired tilted position back to a doughnut removal position in which the angle β is between forty-five degrees (45°) and ninety degrees (90°); and retaining the anvil head assembly in the doughnut removal position.

In some embodiments, the method further includes removing a tissue doughnut from the anvil head assembly when the anvil head assembly is in the doughnut removal position.

In certain embodiments, the method further includes securing the anvil head assembly in the pre-fired tilted position using a suture.

In embodiments, moving the anvil head assembly from the pre-fired tilted position to the operative position includes cutting the suture.

In some embodiments, moving the anvil head assembly from the pre-fired tilted position to the operative position includes urging a plunger of the center rod assembly towards the anvil head assembly to tilt the anvil head assembly from the pre-fired tilted position to the operative position.

In certain embodiments, moving the anvil head assembly from the operative position to the post-fired tilted position includes moving a backup member of the anvil head assembly from a retracted position to an advanced position within a housing of the anvil head assembly.

In embodiments, moving the anvil head assembly from the operative position to the post-fired tilted position includes urging a plunger towards the anvil head assembly to tilt the anvil head assembly from the operative position to the post-fired tilted position.

In some embodiments, moving the anvil assembly from the post-fired tilted position back to the doughnut removal position includes manually pivoting the anvil head assembly to the doughnut removal position.

In certain embodiments, retaining the anvil head assembly in the doughnut removal position includes positioning locking structure of the anvil head assembly in contact with the plunger of the center rod assembly.

Another aspect of the disclosure is directed to a tiltable anvil assembly having and an anvil head assembly and a center rod assembly. The anvil head assembly includes a housing, a post centrally disposed within the housing, a backup plate movably supported about the post from a retracted position to an advanced position, and a cutting ring supported on a proximal surface of the backup plate. The post includes locking structure. The housing defines an annular recess positioned about the post and supports an anvil surface positioned about the annular recess that defines a plane. The center rod assembly includes a center rod defining a longitudinal axis and a plunger supported by the center rod. The center rod has a proximal portion adapted to releasably couple with a circular stapler. The distal portion of the center rod is pivotably coupled to the post of the anvil head assembly by a pivot member such that the anvil head assembly is movable in relation to the center rod between an operative position and a post-fired tilted position. The plane defined by the anvil surface and the longitudinal axis of the center rod defines an angle β, wherein the angle β is ninety degrees when the anvil head assembly is in the operative position and less than thirty degrees when the anvil head assembly is in the post-fired tilted position. The anvil head assembly is movable from the post-fired tilted position to a doughnut removal position, wherein angle β is between forty-five degrees and ninety degrees. The locking structure of the post is configured to engage the center rod assembly to retain the anvil head assembly in the doughnut removal position.

In embodiments, the backup plate includes a finger and the center rod includes a distal portion having an engagement surface. The finger of the backup plate is positioned in contact with the engagement surface of the center rod when the backup plate is in the retracted position to retain the anvil head assembly in the operative position.

In some embodiments, the engagement surface of the center rod includes at least one flat.

In certain embodiments, the locking structure includes an extension that extends proximally from the post towards the center rod.

In embodiments, the extension defines a tapered surface that is positioned to engage the center rod assembly to retain the anvil head assembly in the doughnut removal position.

In some embodiments, the center rod assembly includes a biasing member positioned to urge the plunger into the anvil head assembly to urge the anvil head assembly towards the post-fired tilted position.

In certain embodiments, the extension is positioned to engage the plunger to retain the anvil head assembly in the doughnut removal position.

In embodiments, the anvil assembly includes a cam latch plate supported on the anvil head assembly. The cam latch plate is positioned to engage the backup plate when the backup plate is in the post-fired tilted position to prevent movement of the backup plate from the advanced position back to the retracted position.

In some embodiments, the post defines a transverse slot and the cam latch member is pivotably supported within the transverse slot about the pivot member.

In certain embodiments, in the operative position, the extension is covered by the cam latch member, and in the post-fired position, the extension extends radially outward of the cam latch member.

BRIEF DESCRIPTION OF THE DRAWINGS

Various embodiments of the presently disclosed tiltable anvil assembly are described herein below with reference to the drawings, wherein:

FIG. 4 is an exploded, side perspective view of the tiltable anvil assembly shown in FIG. 1;

FIG. 5 is an enlarged view of the indicated area of detail shown in FIG. 4;

FIG. 6 is a side view of a cam latch member of the tiltable anvil assembly shown in FIG. 4;

FIG. 9 is a side, perspective view of the tiltable anvil assembly shown in FIG. 1 with the anvil head in the operative position;

FIG. 10 is a side cross-sectional view of the tiltable anvil assembly shown in FIG. 9 in the operative position and a distal portion of an anvil retainer of a surgical stapling device shown cutaway positioned within a center rod of the anvil assembly;

DETAILED DESCRIPTION OF EMBODIMENTS

Figure 1:
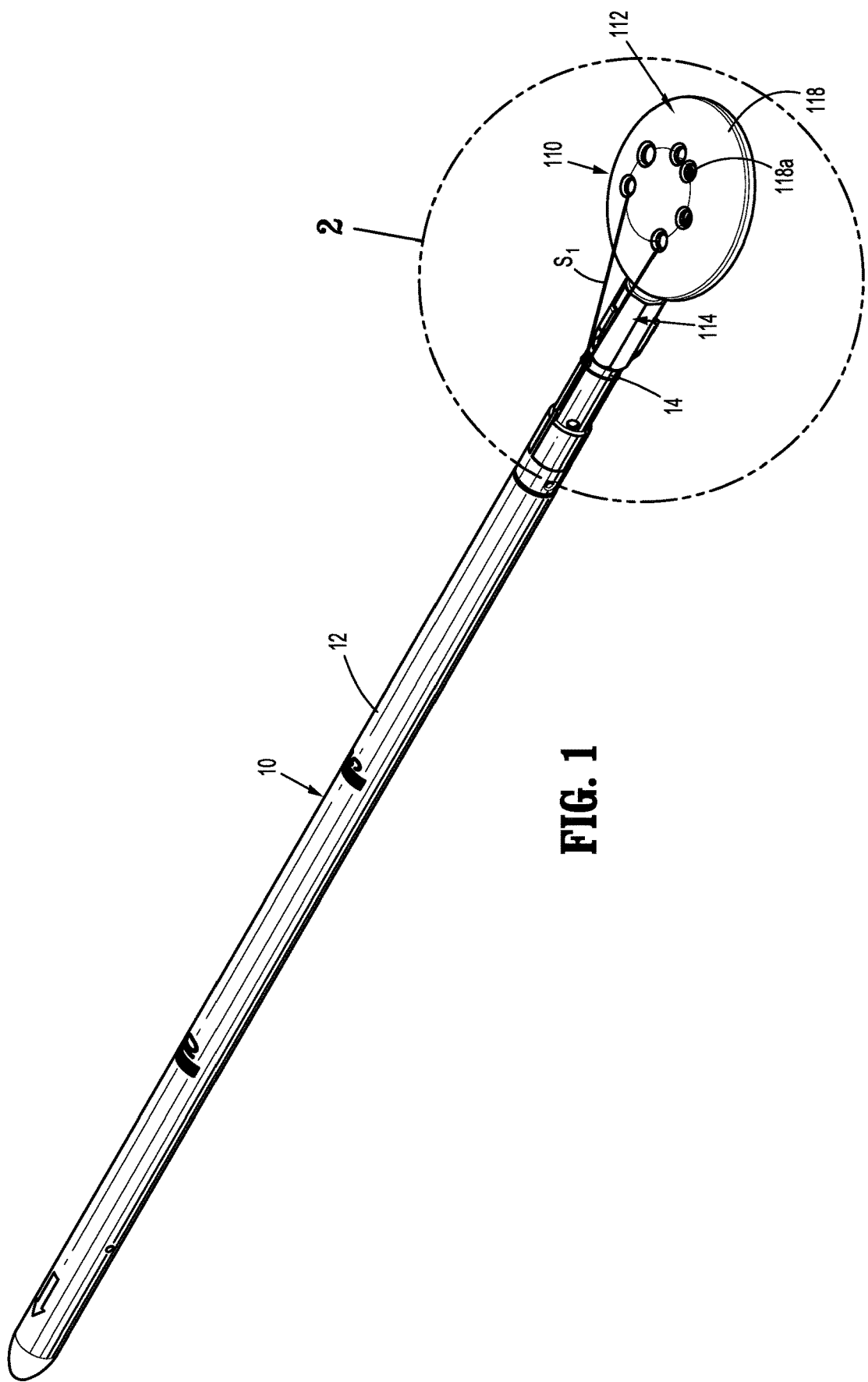
FIG. 1 is a side perspective view from the distal end of an exemplary embodiment of the presently disclosed tiltable anvil assembly supported on an anvil delivery system with the anvil assembly tilted.

The presently disclosed pre-tilted anvil assembly will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula and the term "clinician" is used generally to refer to medical personnel including doctors, nurses, and support personnel.

The presently disclosed tiltable anvil assembly is provided with an anvil head assembly that is tiltable from an operative position to a post-fired tilted position after firing of a circular stapler to minimize the profile of the anvil head assembly during removal of the anvil head assembly from a body lumen of a patient. In order to simplify removal of a tissue doughnut from the anvil head assembly after firing, the anvil assembly includes locking structure to retain the anvil head assembly in a post-fired doughnut removal position. As used herein, the doughnut removal position is a position in which a plane defined by an anvil surface of the anvil head assembly and the longitudinal axis of the anvil assembly define an angle (angle β) between about 45 degrees and about 90 degrees and, in some embodiments is between about 60 degrees and 90 degrees.

In use, after the circular stapler is fired and the anvil assembly is disconnected from the circular stapler, the anvil head assembly automatically pivots from the operative position to a post-fired tilted position by a biasing member to minimize trauma to the patient during removal of the anvil assembly from the lumen of the patient. After the anvil assembly has been removed from the patient, the anvil head assembly can be manually pivoted from the post-fired tilted position to the doughnut removal position to provide access to a tissue doughnut positioned within the anvil head assembly. The locking structure which is described in further detail below is provided on the anvil assembly to retain the anvil head assembly in the doughnut removal position to simplify removal of the tissue doughnut.

Figure 2:
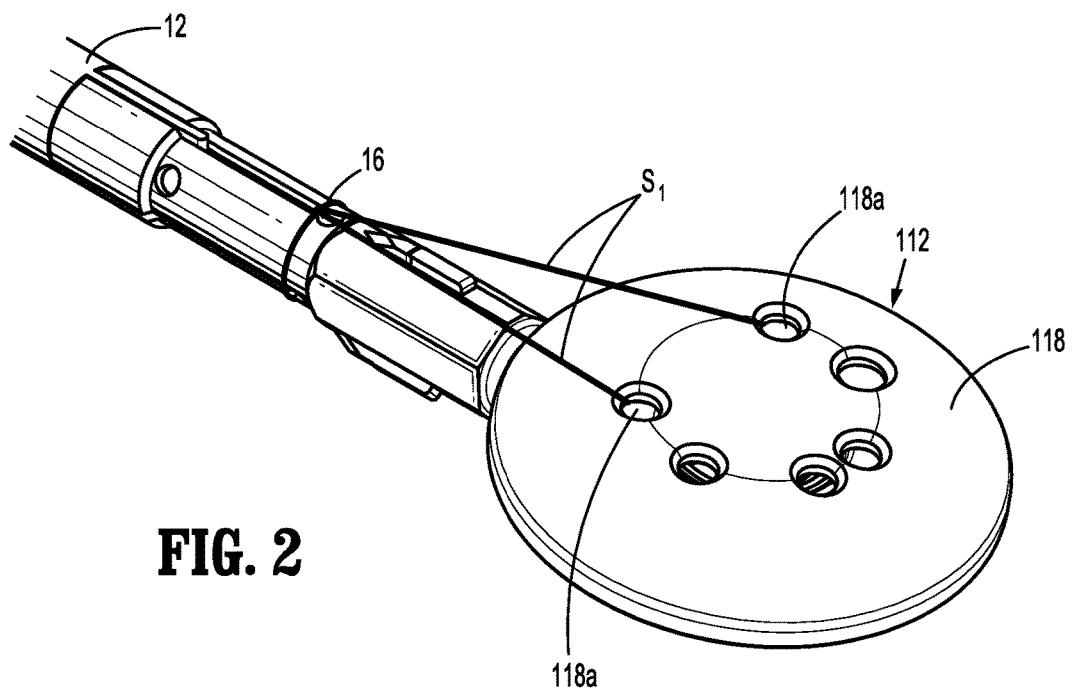
FIG. 2 is an enlarged view of the indicated area of detail shown in FIG. 1.
Figure 3:
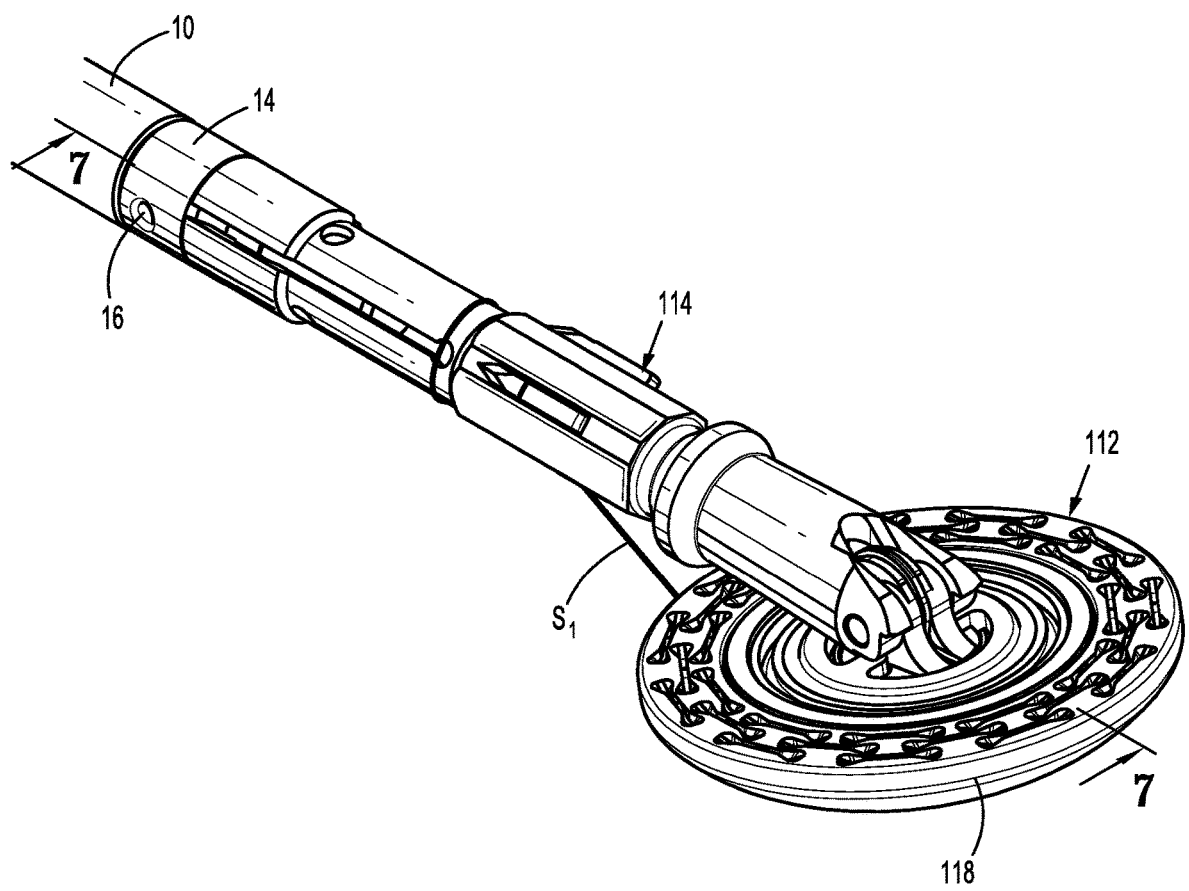
FIG. 3 is a side perspective view of the distal end of the tiltable anvil assembly and anvil delivery system shown in FIG. 1.

FIGS. 1-3 illustrate a side perspective view of an exemplary embodiment of the presently disclosed tiltable anvil assembly, shown generally as anvil assembly 110. The anvil assembly 110 is supported on a distal end of an anvil delivery system 10. The anvil assembly 110 includes an anvil head assembly 112 and a center rod assembly 114. The anvil head assembly 110 includes an anvil head or housing 118 that defines openings 118a. The anvil delivery system 10 includes a flexible tube 12 and an adapter 14. The adapter 14 has a first end fixedly secured to one end of the flexible tube 12 and a second end secured to the center rod assembly 114 by a suture "S1". The adapter 14 defines a through bore 16 (FIG. 2). The suture "S1" is received in the through bore 16 of the adapter 14 of the anvil delivery system 10 and the openings 118a in the housing 118 of the anvil head assembly 112 to secure the anvil head assembly 112 to the anvil delivery system 10 in a pre-fired tilted position. For a more detailed description of the construction and operation of the presently disclosed anvil delivery system 10, see U.S. Publication No. 2015/0366563 ("the '563 Publication") which is incorporated herein by reference in its entirety.

Referring to FIG. 4, the anvil assembly 110 includes an anvil head assembly 112 and a center rod assembly 114. The anvil head assembly 112 includes a post 116, a housing 118, a backup member or plate 120, a cutting ring 122, a cutting ring base 123, an anvil surface 124, a sleeve 125, a cam latch member 126, and a retainer member 127. In embodiments, the post 116 is monolithically formed with and centrally positioned within the housing 118. Alternately, the housing 118 and the post 116 may be formed separately and fastened together using any known fastening technique, e.g., welding or crimping. The anvil surface 124 is supported on the housing 118 about the post 116 and defines a plurality of staple deforming pockets 130 for receiving and deforming staples. The post 116 defines a transverse slot 172 that is described in further detail below.

Referring also to FIG. 5, the post 116 includes locking structure that is configured to retain the anvil head assembly 112 in a doughnut removal position after firing of a circular stapler. In embodiments, the locking structure includes a pair of extensions 131 that extend proximally from the post 116 towards the center rod assembly 114. The extensions 131 define a portion of a transverse slot 172 formed in the post 116 which is described in further detail below. A proximal end of each of the extensions 131 has a tapered surface 132 which is also described in further detail below.

Figure 11:
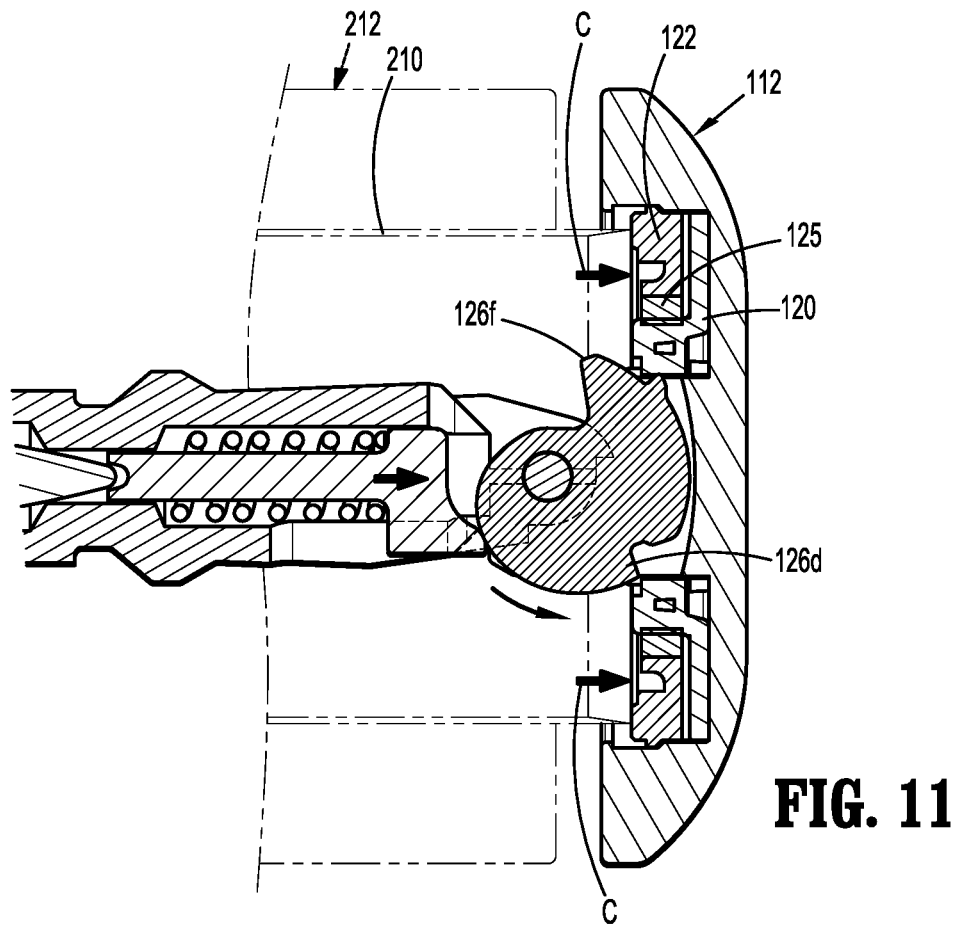
FIG. 11 is a side perspective view of the tiltable anvil assembly shown in FIG. 10 in the operative position and a distal portion of a surgical stapling device shown in phantom as the stapling device is being fired.

The housing 118 of the anvil head assembly 112 defines an inner annular recess 136 positioned between the post 116 and the anvil surface 124. The backup plate 120 of the anvil head assembly 112 includes a central opening 134 that receives the post 116 of the anvil head assembly 112 such that the backup plate 120 is movable within the inner annular recess 136 of the housing 118 between a retracted position (FIG. 10) and an advanced position (FIG. 11). The backup plate 120 includes an annular flange 120a that is positioned about the central opening 134. The backup plate 120 also includes a pair of inwardly extending fingers 138 which are described in further detail below.

The cutting ring 122 defines an opening 122a. The sleeve 125 of the anvil head assembly 112 is fixedly supported within the opening 122a of the cutting ring 122 and defines an opening 125a that has a configuration that corresponds to the configuration of the platform 120a of the backup plate 120. In embodiments, the sleeve 125 is press-fit about the annular flange 120a to secure the sleeve 125 and the cutting ring 122 to the backup plate 120. Alternately, the cutting ring 122 and the sleeve 125 can be of unitary construction and/or the cutting ring 122 can be secured to the backup plate 120 using a variety of fastening techniques. Although the flange 120a is illustrated as having a circular shape, other configurations are envisioned, e.g., square, rectangular, triangular, etc. In embodiments, the cutting ring 122 is formed from polyethylene and the backup plate 120 is formed from a harder material such as a metal, e.g., stainless steel. Alternately other materials of construction may be used to construct backup plate 120 and cutting ring 122. Further, the backup plate 120 and the cutting ring 122 can be formed as a single or unitary structure. The cutting ring 122 is secured to the backup plate 120 such that the cutting ring 122 and the backup plate 120 form an assembly that is slidable about post 116 from the retracted position (FIG. 10) to the distal position (FIG. 11).

In embodiments, a cutting ring base 123 is secured to an inwardly facing surface of the cutting ring 122 using, for example, an adhesive. In one embodiment, the cutting ring base 123 is formed from a material having a hardness that is greater than that of the cutting ring, e.g., mylar. Alternately, it is envisioned that the cutting ring 122 need not have a base 123.

The retainer member 127 is positioned within the inner annular recess 136 of the housing 118 between the backup plate 120 and a back wall 118a of the housing 118. In embodiments, the retainer member 127 is annular and includes a plurality of deformable tabs 127a that engage a distal surface of the backup plate 120. The retainer member 127 is positioned to prevent movement of the backup plate 120 and the cutting ring 122 assembly from the retracted position to the advanced position within the inner annular recess 136 of the housing 118 until a predetermined force sufficient to deform the tabs 127a is applied to the backup plate 120 and cutting ring 122 assembly. The predetermined force can be close to but is less than the force applied by a cutting blade of a circular stapler when the cutting blade engages the cutting ring 122 of the anvil assembly 110 during firing of the circular stapler. In embodiments, the predetermined force is between about ten pounds and about ninety pounds and can be about thirty pounds. When the predetermined force is reached, the backup plate 120 is pressed into the tabs 127a of the retainer 127 such that the tabs 127a are deformed and the backup plate 120 and cutting ring 122 assembly moves towards the advanced position into the inner annular recess 136. It is envisioned that other crushable, deformable, collapsible or movement restricting members may be used to retain the backup plate/cutting ring assembly in a fixed position until the predetermined force has been applied to the backup plate/cutting ring assembly.

Referring to FIGS. 4-7, the cam latch member 126 includes a body 126a having a through bore 126b. The through bore 126b is dimensioned to receive the pivot member 162 of the center rod assembly 114 such that the cam latch member 126 is pivotally mounted within the transverse slot 172 (FIG. 3) of the post 116 about the pivot member 162. The cam latch member 126 includes a first body portion 126c that extends partially from the transverse slot 172 of post 116 in the pre-fired tilted position of the anvil head assembly 112 such that the first body portion 126c of the cam latch member 126 is engaged by the finger 166 of the plunger 154 of the center rod assembly 114. The first body portion 126c is configured such that the distance between the outer edge of the first body portion 126c and the through bore 126b increases in a counter-clockwise direction about the cam latch member 126 as viewed in FIGS. 6 and 7. In this manner, the plunger 154 is able to move distally as the cam latch member 126 rotates in the counter-clockwise direction from the pre-fired tilted position (FIG. 7) to the operative position (FIG. 10).

The cam latch member 126 also includes an edge 126f and a tab 126g. A leading portion of edge 126f is positioned and configured to engage an inner periphery 120b of the backup plate 120 when the anvil head assembly 112 is in the pre-fired tilted position to prevent counter clockwise rotation of the cam latch member 126 prior to firing of the circular stapler as described below. The tab 126g is positioned to engage a distal wall 172a (FIG. 8) of the housing 118 that defines the transverse slot 172 of the post 116 to prevent cam latch member 126 from clockwise rotation of the cam latch member 126 as viewed in FIG. 7 in the pre-fired tilted position.

The anvil center rod assembly 114 includes a center rod 152, a plunger 154, and plunger spring or biasing member 156. A distal end of center rod 152 includes a pair of arms 159 which are spaced from each other to define a cavity 159a. Each arm 159 defines a transverse through bore 158 that is aligned with a central longitudinal axis of center rod 152, a distal flat or engagement surface 152a, and a stop surface 153 that projects distally from the distal end of the center rod 152. Alternately, the through bores 158 can be offset from the longitudinal axis of center rod 152. The post 116 of the anvil head assembly 112 is dimensioned and configured to be positioned within the cavity 159a and also defines a transverse through bore 116a. A pivot member 162 is positioned through the through bores 158 of the center rod 152 and the through bore 116a of the post 116 of the anvil head assembly 112 to pivotally secure the post 116 of the anvil head assembly 112 to the center rod 152 of the center rod assembly 114 such that the anvil head assembly 112 is pivotally secured to center rod assembly 114. The plunger 154 includes a finger 166 that is discussed in further detail below.

With continued reference to FIG. 4, a proximal end of the center rod 152 includes a plurality of flexible arms 180 that define a bore 182. The flexible arms 182 each include an opening 180a that is dimensioned to receive a projection formed on or connected to a trocar (not shown) to secure the trocar to the center rod 152. Alternatively, the openings 180a may receive a suture (not shown) for permitting retrieval of anvil assembly 110 from a surgical site. The proximal end of each of the flexible arms 182 includes an internal shoulder 184 (FIG. 7) that is dimensioned to releasably engage an anvil retainer or trocar 200 (FIG. 10) of a circular stapler (not shown) to secure anvil assembly 110 to the circular stapler. A plurality of splines 186 are formed about the center rod 152. The splines 186 function to align the anvil assembly 110 with a staple holding portion of the circular stapler as is known in the art. See, e.g., U.S. Pat. No. 7,303,106 ("the '106 patent") which is incorporated herein in its entirety by reference.

The plunger 154 of the center rod assembly 114 is slidably positioned in a bore 164 (FIG. 7) formed in the first end of center rod 152. The engagement finger 166 of the plunger 154 is offset from the pivot axis of anvil head assembly 112 and, as discussed above, is biased into engagement with the outer edge of the body portion 126c of cam latch member 126 by the biasing member 156. The engagement of finger 166 with outer edge of the body portion 126c of cam latch member 126 urges the cam latch member 126 in the counter-clockwise direction to urge the edge 126f of the cam latch member 126 against the inner periphery 120b of the back plate 120 to urge the anvil head assembly 112 from the pre-fired tilted position towards the operative position on center rod 152.

Figure 7:
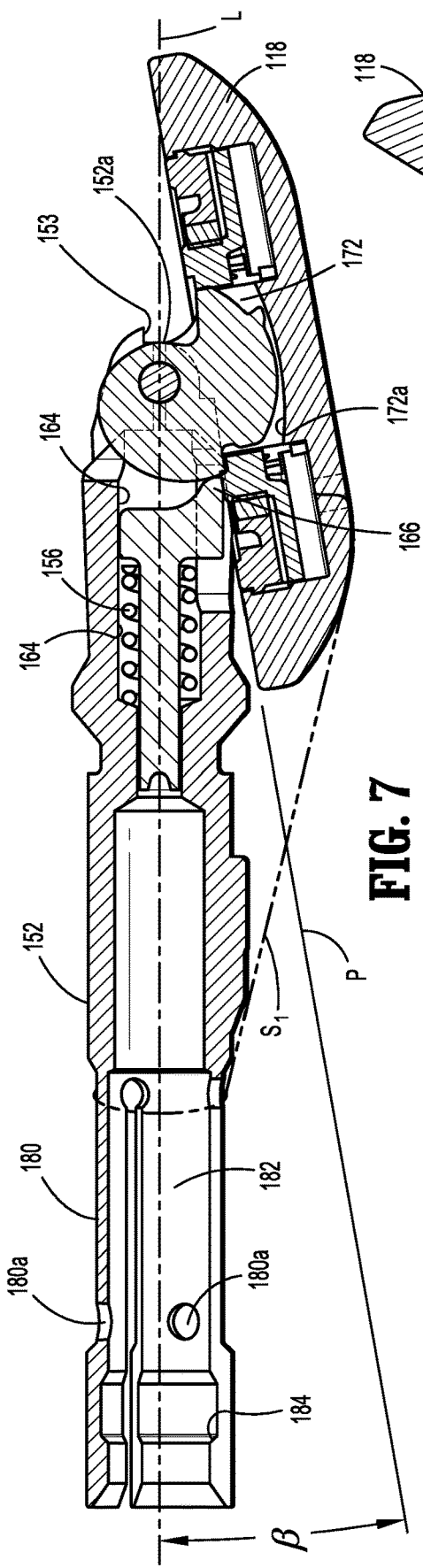
FIG. 7 is a cross-sectional view taken along section line 7-7 of FIG. 3.

Referring to FIG. 7, the suture S1 secures the anvil head assembly 112 in the pre-fired tilted position against the urging of the biasing member 156. More specifically, in the pre-fired tilted position of the anvil assembly 110, a plane "P" defined by the anvil surface 124 defines an acute angle β with the longitudinal axis "L" of the center rod 152. In this position, the finger 166 of the plunger 1154 is engaged with the outer edge of the body portion 126c of the cam latch member 126 and the plunger 154 is urged distally by the biasing member 156 to urge the anvil head assembly 112 and cam latch member 126 towards the operative position. In the pre-fired tilted position, angle β can define an angle of less than about thirty degrees (30°). It is envisioned that angle β may be greater than about thirty degrees (30°) depending on the surgical procedure being performed.

Figure 8:
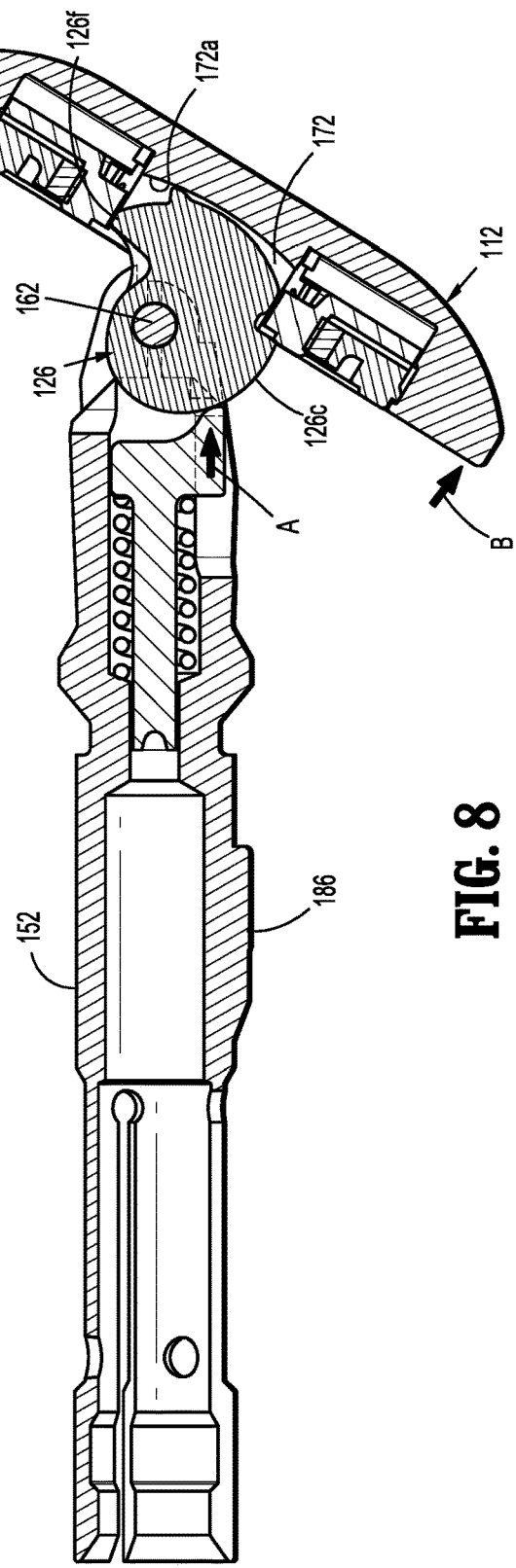
FIG. 8 is a side cross-sectional view of the tiltable anvil assembly shown in FIG. 7 as an anvil head of the anvil assembly moves from the pre-tilted position towards the operative position.

Referring to FIG. 8, when the suture S1 is cut by a clinician using, for example, scissors or a scalpel (not shown), the plunger 154 is moved distally in the direction indicated by arrow "A" by the biasing member 156 to urge the cam latch member 126 and the anvil head assembly 112 in the direction indicated by the arrow "B" towards the operative position. As the cam latch member 126 rotates about the pivot member 162, the finger 166 of the plunger 154 of the center rod assembly 114 slides along the outer edge of the body portion 126c of the cam latch member 126.

Figure 13:
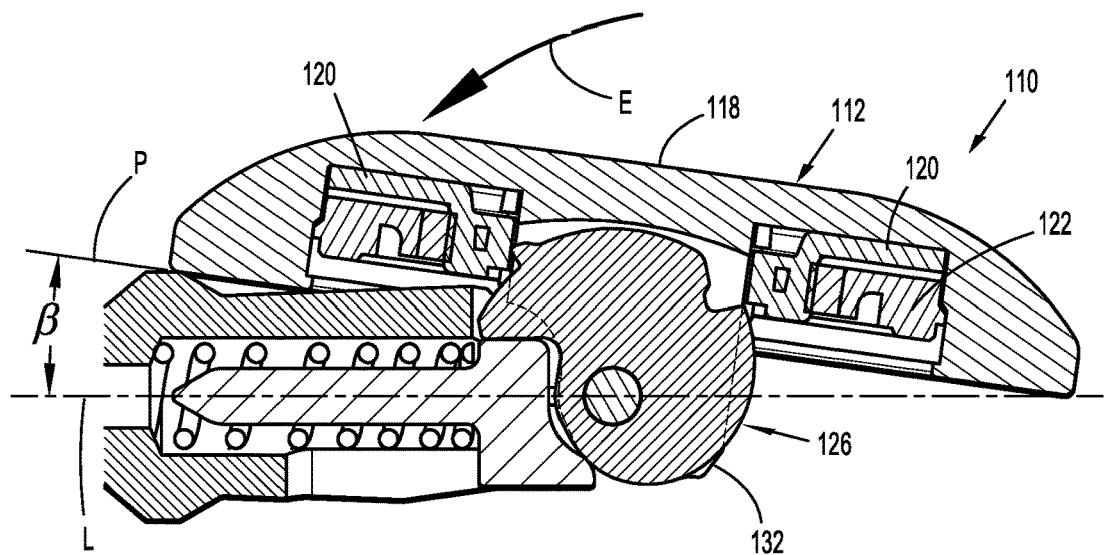
FIG. 13 is a side cross-sectional view of the tiltable anvil assembly shown in FIG. 12 in the fired and tilted position.

Referring to FIGS. 9 and 10, in the pre-fired operative position of anvil head assembly 112 and the cam latch member 126, the fingers 138 of the backup plate 120 are positioned atop the flats 152a defined on the distal end of the center rod 152 and are engaged with the stop surfaces 153 that extend distally from a the distal end of the center rod 152. Engagement of the fingers 138 with the flats 152a and the stop surfaces 153 of the center rod 152 retains the anvil head assembly 112 in the operative position and prevents the biasing member 156 from urging the anvil head assembly 112 beyond the operative position towards a post-fired tilted position (FIG. 13). In the operative position, the plane "P" defined by the anvil surface 124 is substantially perpendicular to the longitudinal axis "L" defined by the center rod 152 (FIG. 10.)

Referring to FIG. 10, when the anvil assembly 110 is secured to a circular stapler (only the anvil retainer or trocar 200 of the circular stapler is shown), the trocar 200 of the circular stapler is inserted into the bore 182 defined by the flexible arms 180 of the center rod 152. When the trocar 200 is fully inserted into the bore 182, a distal end of the trocar 200 engages the proximal end of the plunger 154 such that the plunger 154 is locked in an advanced position. In the advanced position of the plunger 154 with the circular stapler in a pre-fired state, the anvil head assembly 112 is locked in the operative position (FIG. 10).

In use, the anvil assembly 110 is delivered to a surgical site using the anvil delivery system 10. For a detailed description of this procedure, see the '563 Publication. After the anvil assembly 110 is properly positioned at the surgical site, the suture S1 can be cut to release the anvil head assembly 112 and the allow the anvil head assembly 112 and the cam latch member 126 to pivot about the pivot member 162 from the pre-fired tilted position (FIG. 7) to the operative position (FIG. 8) as discussed above. Alternately, the anvil assembly 110 can be delivered to the surgical site using a variety of insertion techniques and tools. In addition, the anvil assembly can be delivered to the surgical site with the anvil assembly in the operative position.

Figure 12:
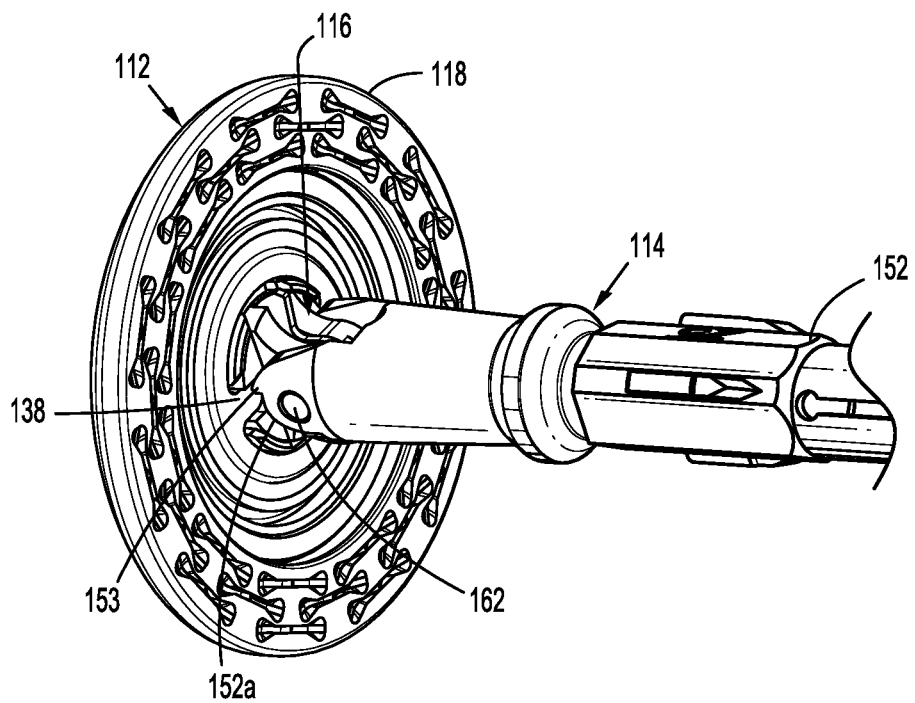
FIG. 12 is a perspective view from a proximal end of the tiltable anvil assembly shown in FIG. 11 in the operative position after a backup ring of the anvil assembly is pushed distally into a housing of the anvil head assembly.

Referring to FIGS. 11 and 12, when the circular stapler (not shown) is fired to advance staples into the anvil surface 124 through tissue (see the '106 patent for a detailed description of this operation), an annular knife 210 of a shell assembly 212 (FIG. 11) is advanced in the direction indicated by arrows "C" in FIG. 11 into contact with the cutting ring 122 to advance the cutting ring 122 and backup plate 120 assembly further into the annular recess 136 of the housing 118 of the anvil head assembly 112. As the backup plate 120 advances into the annular recess 136, the fingers 138 of the backup plate 120 move to a position spaced distally of the flats 152a and the stop surfaces 153 of the center rod 152. As this occurs, the plunger 154 rotates the cam latch member 126 in the direction indicated by arrow "D" in FIG. 11 such that the portion of the cam latch member 126 defining the edge 126f moves to a position proximally of the backup plate 120. This positioning of the cam latch member 126 prevents proximal movement of the backup plate 120 when the annular knife 210 is retracted after firing of the circular stapler. It is noted that the tab 126g of the cam latch member 126 is rotated to a position spaced from the distal wall 172a defining the transverse slot 172 and is positioned in contact with the backup plate 120. Proximal movement of the backup plate 120 could reposition the fingers 138 of the backup plate 120 onto the flats 152a of the center rod 152 and obstruct pivotal movement of the anvil head assembly 112 from the operative position to the post-fired tilted position (FIG. 13). A second portion 126d (FIG. 11) of the cam latch member 126 also engages an opposite side of the backup plate 120 to prevent retraction of the backup plate 120 with the annular knife 210.

Referring to FIG. 13, when the anvil head assembly 112 is moved to a position spaced from the shell assembly 212 (FIG. 11), the biasing member 156 of the center rod assembly 114 will pivot the anvil head assembly 112 in the direction indicated by arrow "E" in FIG. 13 to the post-fired tilted position. In the post-fired tilted position, similar to the pre-fired tilted position, angle β can define an angle of less than about thirty degrees (30°). It is envisioned that angle β may be greater than about thirty degrees (30°) depending on the surgical procedure being performed. As discussed above, in the post-fired tilted position, the anvil head assembly 112 has a reduced profile such that the anvil assembly 110 can be removed from a body lumen of a patient with minimal trauma to the patient.

Figure 14:
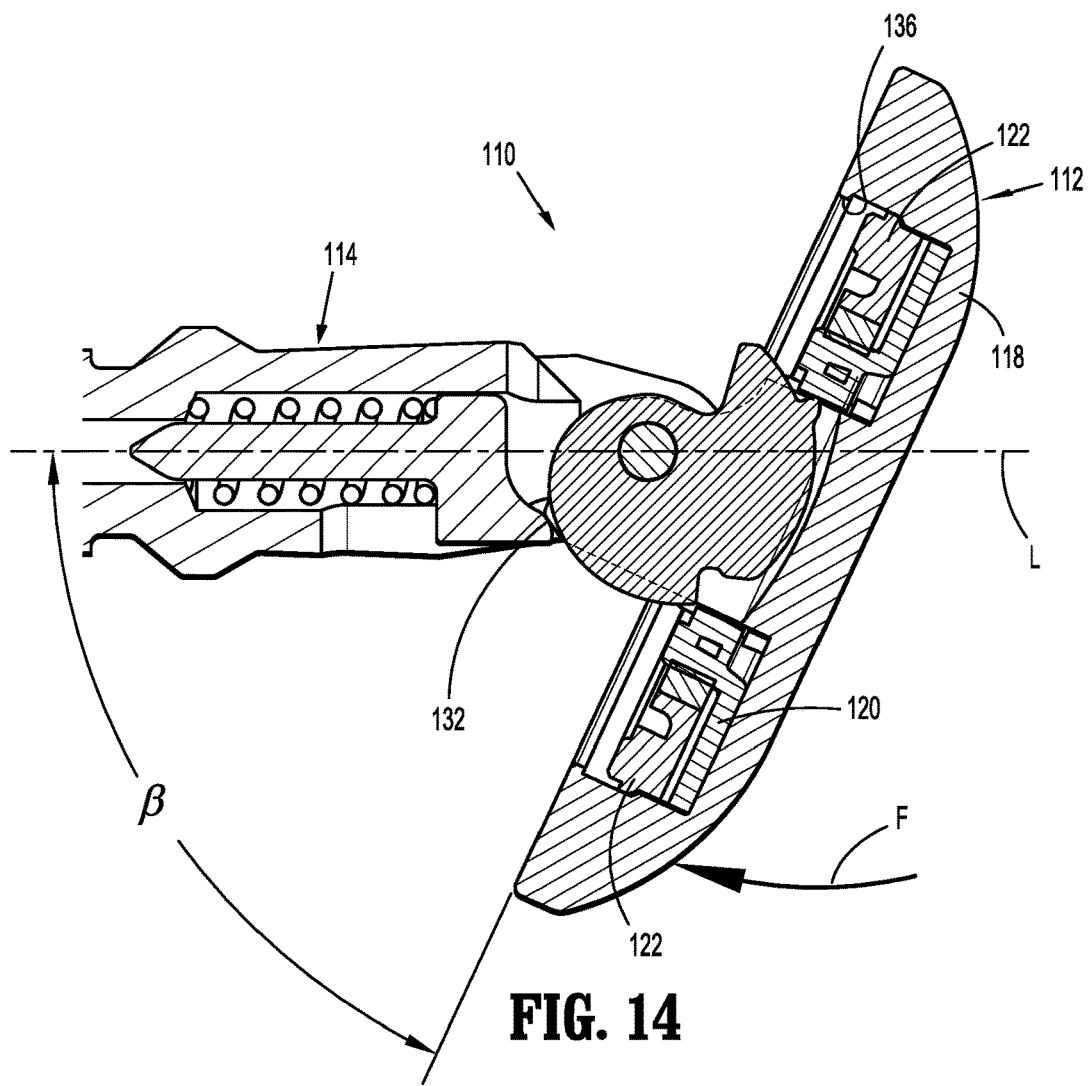
FIG. 14 is a side cross-sectional view of the tiltable anvil assembly shown in FIG. 13 in the fired and tilted position as the anvil head assembly is partially rotated back towards the operative position.
Figure 14A:
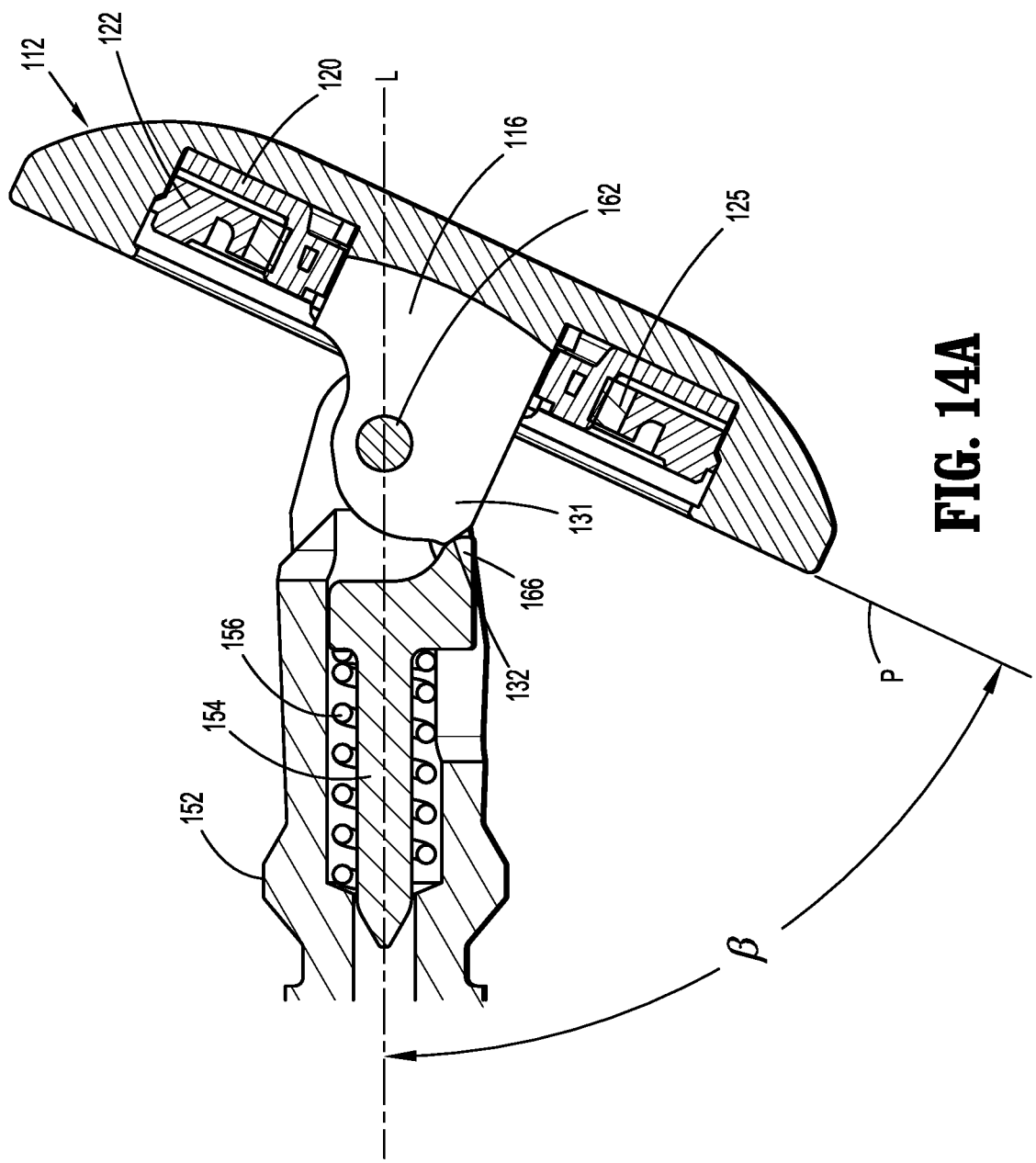
FIG. 14A is a side cross-sectional view of the tiltable anvil assembly shown in FIG. 13 in the fired and tilted position with the cam latch member removed as the anvil head assembly is partially rotated back towards the operative position.
Figure 15:
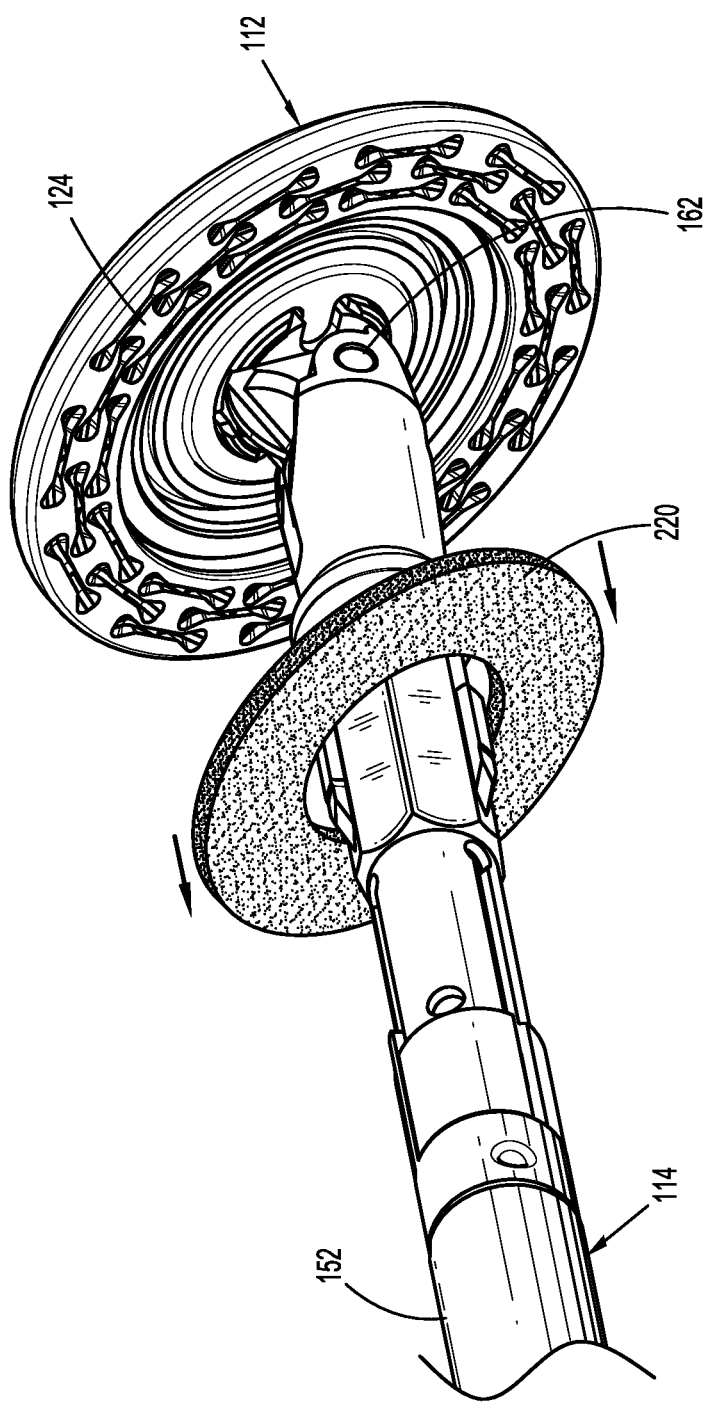
FIG. 15 is a side perspective view of the tiltable anvil assembly shown in FIG. 13 in the fired and tilted position as the anvil head assembly is partially rotated back towards the operative position and a tissue doughnut is removed from the housing of the anvil head assembly.

Referring to FIGS. 14-15, as is known in the art, when a circular stapler is fired that includes an annular knife such as annular knife 210 (FIG. 13), a tissue doughnut 220 (FIG. 15) is cut in the tissue being treated. The tissue doughnut 220 is positioned in the annular recess 136 of the housing 118 between the shell assembly 212 (FIG. 11) and the cutting ring 122. When the anvil head assembly 112 is in the post-fired tilted position, it is difficult to remove the tissue doughnut 220 from the anvil head assembly 112. In order to simplify removal of the tissue doughnut 220, the locking structure including the extensions 131 of the post 116 are positioned to engage the finger 166 of the plunger 152 to retain the anvil head assembly 112 in a doughnut removal position to provide greater access to the tissue doughnut. As discussed above, in the doughnut removal position, angle β is between about 45 degrees and about 90 degrees. In certain embodiments, angle β is between about 60 degrees and about 90 degrees.

More specifically, after the anvil assembly 110 is removed from a patient, a clinician can manually tilt the anvil head assembly 112 back towards the operative position in the direction indicated by arrow "F" in FIG. 14 to the doughnut removal position. It is noted that with the cam latch member 126 rotated to the position shown in FIG. 13, the tapered surfaces 132 of the extensions 131 extend radially outwardly of the cam latch member 126. Thus, when the anvil head assembly 112 is rotated in the direction indicated by arrow "F", the extensions 131 on the post 116 approach and engage the finger 166 of the plunger 154 of the center rod assembly 114. When the tapered surfaces 132 of the extensions 131 engage the finger 166 of the plunger 154, the tapered surfaces 132 cam the plunger 154 downwardly such that a portion of the extensions 131 passes over the finger 166 and engages the finger 166 at a position between the outer surface of the finger 166 and the longitudinal axis of the center rod 152. This engagement between the extensions 131 and the finger 166 of the plunger 154 retains the anvil head assembly 112 in the doughnut removal position (FIG. 15.) Although the extensions 131 are shown to be configured to retain the anvil head assembly 112 in a position between the pre-fired tilted position and the operative position, it is envisioned that the configuration of the extensions 131 and the cam latch member 126 could be modified to retain the anvil head assembly 112 in a variety of different positions between the pre-fired and the post-fired tilted positions.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A method of treating tissue comprising:
   inserting an anvil assembly including an anvil center rod assembly and an anvil head assembly into a vessel lumen in a pre-fired tilted position in which a plane defined by an anvil surface of the anvil head assembly and a longitudinal axis of the anvil center rod assembly define an angle β of less than thirty degrees (30°);
   moving the anvil head assembly from the pre-fired tilted position to an operative position in which the angle β is ninety degrees (90°);
   clamping tissue between the anvil head assembly and a staple cartridge of a circular stapler;
   firing the circular stapler to advance staples through the tissue and into the anvil head assembly and cutting the tissue with an annular knife;
   moving the anvil head assembly from the operative position to a post-fired tilted position in which the angle β is less than thirty degrees (30°);
   moving the anvil head assembly from the post-fired tilted position back to a doughnut removal position in which the angle β is between forty-five degrees (45°) and ninety degrees (90°); and
   retaining the anvil head assembly in the doughnut removal position.

2. The method of claim 1, further including removing a tissue doughnut from the anvil head assembly when the anvil head assembly is in the doughnut removal position.

3. The method of claim 1, further including securing the anvil head assembly in the pre-fired tilted position using a suture.

4. The method of claim 3, wherein moving the anvil head assembly from the pre-fired tilted position to the operative position includes cutting the suture.

5. The method of claim 4, wherein moving the anvil head assembly from the pre-fired tilted position to the operative position includes urging a plunger of the center rod assembly towards the anvil head assembly to tilt the anvil head assembly from the pre-fired tilted position to the operative position.

6. The method of claim 5, wherein moving the anvil head assembly from the operative position to the post-fired tilted position includes moving a backup member of the anvil head assembly from a retracted position to an advanced position within a housing of the anvil head assembly.

7. The method of claim 6, wherein moving the anvil head assembly from the operative position to the post-fired tilted position includes urging a plunger towards the anvil head assembly to tilt the anvil head assembly from the operative position to the post-fired tilted position.

8. The method of claim 1, wherein moving the anvil head assembly from the post-fired tilted position back to the doughnut removal position includes manually pivoting the anvil head assembly to the doughnut removal position.

9. The method of claim 1, wherein retaining the anvil head assembly in the doughnut removal position includes positioning locking structure of the anvil head assembly in contact with the plunger of the center rod assembly.

10. A tiltable anvil assembly comprising:
an anvil head assembly including a housing, a post centrally disposed within the housing and including locking structure, an annular recess positioned about the post, an anvil surface defining a plane positioned about the annular recess, a backup plate movably supported about the post from a retracted position to an advanced position, and a cutting ring supported on a proximal surface of the backup plate; and
a center rod assembly including a center rod defining a longitudinal axis and a plunger supported by the center rod, the center rod having a proximal portion adapted to releasably couple with a circular stapler, the distal portion of the center rod being pivotably coupled to the post of the anvil head assembly by a pivot member such that the anvil head assembly is movable in relation to the center rod between an operative position and a post-fired tilted position, the plane defined by the anvil surface and the longitudinal axis of the center rod defining an angle $\beta$, wherein the angle $\beta$ is ninety degrees when the anvil head assembly is in the operative position and the angle $\beta$ is less than thirty degrees when the anvil head assembly is in the post-fired tilted position;
wherein the anvil head assembly is movable from the post-fired tilted position to a doughnut removal position in which angle $\beta$ is between forty-five degrees and ninety degrees, the locking structure of the post being configured to engage the center rod assembly to retain the anvil head assembly in the doughnut removal position.

11. The tiltable anvil assembly of claim 10, wherein backup plate includes a finger and the center rod includes a distal portion having an engagement surface, the finger of the backup plate being positioned in contact with the engagement surface of the center rod when the backup plate is in the retracted position to retain the anvil head assembly in the operative position.

12. The tiltable anvil assembly of claim 11, wherein the engagement surface of the center rod includes at least one flat.

13. The tiltable anvil assembly of claim 12, wherein the locking structure includes an extension that extends proximally from the post towards the center rod.

14. The tiltable anvil assembly of claim 13, wherein the extension defines a tapered surface that is positioned to engage the center rod assembly to retain the anvil head assembly in the doughnut removal position.

15. The tiltable anvil assembly of claim 14, wherein the center rod assembly includes a biasing member positioned to urge the plunger into the anvil head assembly to urge the anvil head assembly towards the post-fired tilted position.

16. The tiltable anvil assembly of claim 15, wherein the extension is positioned to engage the plunger to retain the anvil head assembly in the doughnut removal position.

17. The tiltable anvil assembly of claim 13, further including a cam latch plate supported on the anvil head assembly, the cam latch plate being positioned to engage the backup plate when the backup plate is in the post-fired tilted position to prevent movement of the backup plate from the advanced position back to the retracted position.

18. The tiltable anvil assembly of claim 17, wherein the post defines a transverse slot, the cam latch member being pivotably supported within the transverse slot about the pivot member.

19. The tiltable anvil assembly of claim 18, wherein in the operative position, the extension is covered by the cam latch member, and in the post-fired tilted position, the extension extends radially outward of the cam latch member.

* * * * *